United States Patent [19]

Zimmer et al.

[11] Patent Number: 4,996,227

[45] Date of Patent: Feb. 26, 1991

[54] 3-(HETEROARYLALKYENE)- AND 3-(ARYLALKYLENE)-2,4(3H,5H)-HETEROCYCLIC DIONES AS CANCER CHEMOTHERAPY DRUGS

[75] Inventors: Hans W. Zimmer, Cincinnati, Ohio; Orlando J. Martelo, Plattsburg, N.Y.; Robert S. Franco, Cincinnati, Ohio

[73] Assignee: University of Cincinnati, Cincinnati, Ohio

[21] Appl. No.: 316,591

[22] Filed: Feb. 24, 1989

Related U.S. Application Data

[63] Continuation-in-part of Ser. No. 878,811, Jun. 26, 1986, abandoned.

[51] Int. Cl.$^5$ .............................................. A61K 31/38
[52] U.S. Cl. .................................................... 514/444
[58] Field of Search ........................ 514/444, 461, 422

[56] References Cited

PUBLICATIONS

Zimmer, et al, Condensation of 2,4(3H,5H) Furandiones with Heteroaromatic Aldehydes, Journal of Heterocyclic Chemistry, vol. 20, p. 787 (May–Jun., 1983).

Primary Examiner—Alan Siegel
Attorney, Agent, or Firm—Frost & Jacobs

[57] ABSTRACT

Heterocyclic diones of the class containing 3-(heteroarylalkylene)- and 3(arylalkylene)-2, 4 (3H, 5H)-furandiones, and 3-(heteroarylalkylene)-pyrrolidene diones and -thiophene diones are disclosed as being effective cancer chemotherapy drugs, some of which are themselves novel compounds. Various members of this class were tested both in vitro and in vivo to demonstrate their effectiveness at reducing or inhibiting cancer tumor cells. The class of drugs was evaluated against a series of 10 human tumors in the in vitro Human Tumor Cell Assay procedure. The procedure indicates that this class of heterocyclic diones is effective against a broad variety of types of cancer and has little or no toxic effects based upon hematological and pathological evaluations.

4 Claims, No Drawings

3-(HETEROARYLALKYENE)- AND 3-(ARYLALKYLENE)-2,4(3H,5H)-HETEROCYCLIC DIONES AS CANCER CHEMOTHERAPY DRUGS

This application is a continuation-in-part of application Ser .No. 06/878,811 filed June 26, 1989, in the names of the same inventors now abandoned.

BACKGROUND OF THE INVENTION

1. Field of the Invention

The present invention pertains to a family of heterocyclic dione compounds employed as cancer chemotherapy drugs. In particular, the present invention concerns employing heterocyclic diones for treating tumors in mammals. Specifically, the furandiones of the class 3-(heteroarylalkylene)- and 3-(arylalkylene)-2,4(3H,5H) furandiones, and 3-(heteroarylalkylene)2,4(3H,5H)-pyrrolidene diones and -thiophenediones are exposed to mammal cancer tumor cells in vitro, or may be injected into or given orally to mammals having cancer tumor cells, at an effective dosage concentration to reduce or eliminate the cancer tumor cells.

2. Prior Art

Treatment of various types of cancer with certain chemotherapy drugs is a well known procedure Some forms of cancer can be treated effectively, even cured, with current chemotherapy drugs. However, many of the most common forms of cancer with high mortality rates (e.g. lung and colon cancer) are almost completely resistant to the current generation of drugs. Accordingly, there is a need for better, more effective cancer chemotherapy drugs which are applicable against many types of cancer and have acceptable side effects.

The use of certain lignans as cancer chemotherapy drugs is well known. In attempting to make analogs of these lignans, applicants discovered the new family of compounds 3-(heteroarylalkylene)-and 3-(arylalkylene)-2,4 (3H,5H)-furandiones, and 3-(heteroarylalkylene)2,4(3H,5H)-pyrrolidiene diones and -thiophenediones. See *Condensation of 2.4(3H5H) Furandiones with Heteroaromatic Aldehydes*, published in the Journal of Heterocyclic Chemistry, Vol 20, page 787, May–June, 1983. At the time these compounds were synthesized, the suggested use of the compounds was as a potential synthetic intermediate for the synthesis of antineoplastic lignans. No other suggested use or further characteristics of the furandione compounds were known to enable one to predict their usefulness.

SUMMARY OF THE INVENTION

The present invention relates to methods for treating mammal tumor cells, including human tumor cells, by treatment with 3-(heteroarylalkylene)- and 3-(arylalkylene)-2,4(3H,5H)-furandiones,-pyrrolidiene diones and -thiophenediones and the synthesis of compounds of this class thought to be novel. The methods include an "in vivo" procedure as well as an "in vitro" procedure. The in vitro procedure calls for obtaining a tissue culture of human cancerous tumor cells and exposing the tumor cells to at least one of the 3-(heteroarylalkylene)- and 3-(arylalkylene)-2,4(3H,5H)-furandiones, and 3-(heteroarylalkylene)2,4(3H,5H)-pyrrolidiene diones and -thiophenediones at a desired concentration for one hour. After treatment, the drug(s) (e.g., furandione(s)) is/are washed from the cells and the cells are cultured in an agar solution and permitted to grow and form colonies for about one to two weeks. At the end of this time, the formed colonies are enumerated under a microscope and compared to the colonies formed from untreated control cells so that the percentage of growth after exposure to the drug may be calculated.

In the in vivo procedure, the drug was injected into healthy mice intraperitoneally to give calculated plasma concentrations of 1, 10 and 100 micrograms per milliliter (mcg/ml). Full pathological evaluation of these animals indicates that the 3-(heteroarylalkylene)- and 3-(arylalkylene)-2,4(3H,5H)-furandiones, and 3-(heteroarylalkylene)2,4(3H,5H)-pyrrolidiene diones and -thiophenediones are not unduly toxic at dosages which the in vitro studies indicate to be effective in inhibiting the proliferation of malignant tumor cells, particularly at the concentration of 10 mcg/ml.

In the broadest sense, the present invention comprises an in vitro testing of cancerous human tumor cells of the class consisting of breast tumors, ovary tumors, stomach tumors, sarcoma tumors, thymus tumors and colon tumors, by obtaining a portion of these tumor cells, adding an effective amount of at least one of the 3-(heteroarylalkylene)- and 3-(arylalkylene)-2,4(3H,5H)-furandiones, and/or 3-(heteroarylalkylene)2,4(3H,5H)-pyrrolidiene diones and -thiophenediones to the tumor cells, permitting the reaction between said heterocyclic dione(s) and the tumor cells to proceed for one hour; and determining the colony growth.

The broadest sense of the present invention also comprises administering at least one heterocyclic dione of the group consisting of 3-(heteroarylalkylene)- and 3-(arylalkylene)-2,4(3H,5H)-furandione, and/or 3-(heteroarylalkylene)2,4(3H,5H)-pyrrolidiene diones and -thiophenediones intraperitoneally into mammals having cancer cells at an effective dosage concentration and determining the effectiveness of said heterocyclic dione(s) against the tumor cells after a predetermined period of time.

DESCRIPTION OF THE PREFERRED EMBODIMENTS

Of the compounds of the present invention, the subclass of 3-(heteroarylalkylene)-2, 4 (3H, 5H) furandiones are generally represented by the following formula:

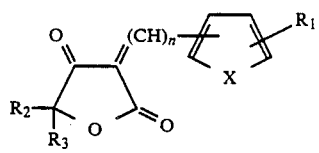

where $R_1$ represents hydrogen, carboxyl, ethoxycarbonyl, methoxy, N-piperidenyl, morpholino, alkyls containing 1 to 3 carbon atoms such as methyl, ethyl and propyl, or halogens such as chlorine, fluorine, bromine, and iodine; and $R_2$ and $R_3$ represent, independently, hydrogen or methyl; and X represents oxygen, sulfur or an amine; and n is 1 or 3.

For example, the 3-(heteroarylalkylene)-2, 4-(3H, 5H) furandiones include

3[(5-methyl-2-thienyl) methylene]-2,4(3H,5H)-furandione;

3-[(3-methyl-2-thienyl) methylene]-2,4(3H,5H)-furandione;

3-(2-furanyl-2-propenylidene)-2,4(3H,5H) -furandione; and

3-[(1-methyl-1H-pyrol-2-yl) methylene]-2,4(3H,5H)-furandione,
3-[(1-methyl-1H-pyrrol-2-yl)methylene]2,4(3H,5H)-furandione,
3-[(5-piperidenyl-2-thienyl)methylene]2,4(3H,5H)-furandione,
3-[(5-carboxyl-2-thienyl)methylene]2,4(3H,5H)-furandione,
3-[(5-ethoxycarbonyl-2-thienyl)methylene]2,4(3H,5H)-furandione,
3-[(5-N-morpholino-2-thienyl)methylene]2,4(3H,5H)-furandione,
3-[(5-iodo-2-thienyl)methylene]2,4(3H,5H)-furandione,
3-[(5-bromo--2-thienyl)methylene]2,4(3H,5H)-furandione,
3-[(3-methyl-2-thienyl)methylene]2,4(3H,5H)-furandione,
3-[(5-methyl-2-thienyl)propenylidene]2,4(3H,5H)-furandione,
3[(5-bromo-2-thienyl)propenylidene]2,4(3H,5H)-furandione,
3[(5-methyl-2-thienyl)methylene]-5,5dimethyl-2,4(3H,5H) furandione,
3[(5-iodo-2-thienyl)methylene]-5,5dimethyl-2,4(3H,5H) furandione,
3[(5-bromo-2-thienyl)methylene]-5,5dimethyl-2,4(3H,5H) furandione,
3[(5-carboxy-2-thienyl)methylene]-5,5dimethyl-2,4(3H,5H) furandione, and
3[(3-methyl-2-thienyl)methylene]-5,5dimethyl-2,4(3H,5H) furandione, the structural formulae of which are as follows:

(4)

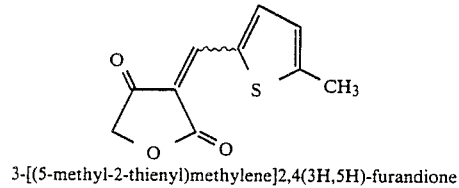

3-[(5-methyl-2-thienyl)methylene]2,4(3H,5H)-furandione (51)

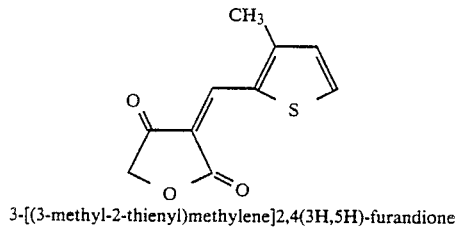

3-[(3-methyl-2-thienyl)methylene]2,4(3H,5H)-furandione

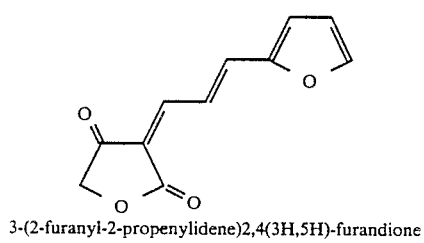

3-(2-furanyl-2-propenylidene)2,4(3H,5H)-furandione

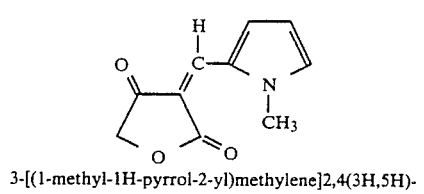

3-[(1-methyl-1H-pyrrol-2-yl)methylene]2,4(3H,5H)-furandione

-continued (68)

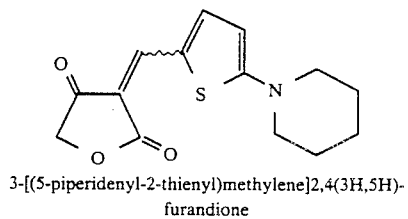

3-[(5-piperidenyl-2-thienyl)methylene]2,4(3H,5H)-furandione (50)

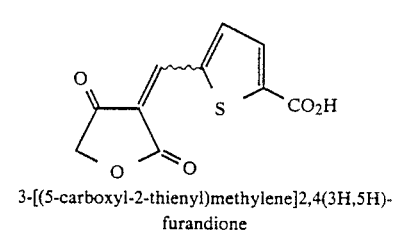

3-[(5-carboxyl-2-thienyl)methylene]2,4(3H,5H)-furandione (45)

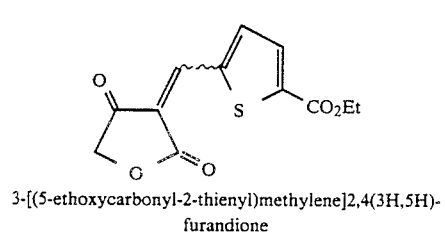

3-[(5-ethoxycarbonyl-2-thienyl)methylene]2,4(3H,5H)-furandione (56)

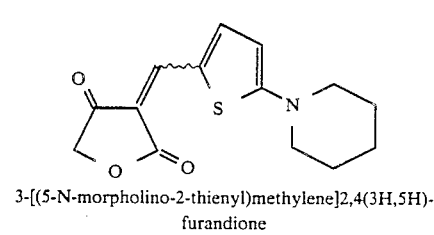

3-[(5-N-morpholino-2-thienyl)methylene]2,4(3H,5H)-furandione (48)

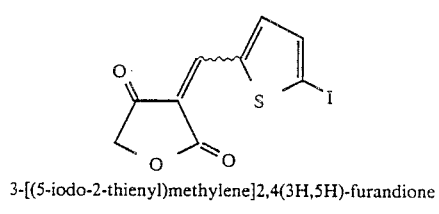

3-[(5-iodo-2-thienyl)methylene]2,4(3H,5H)-furandione (49)

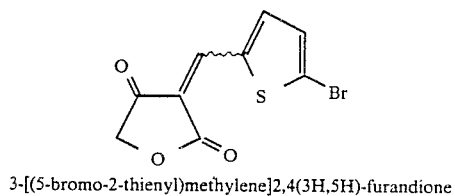

3-[(5-bromo-2-thienyl)methylene]2,4(3H,5H)-furandione (51)

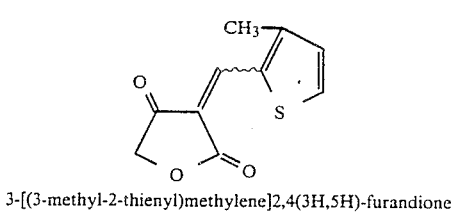

3-[(3-methyl-2-thienyl)methylene]2,4(3H,5H)-furandione

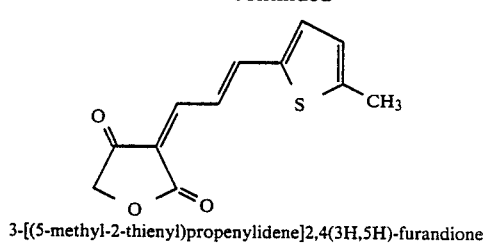

3-[(5-methyl-2-thienyl)propenylidene]2,4(3H,5H)-furandione

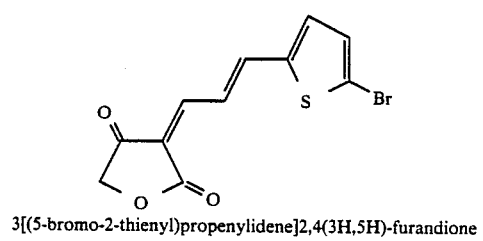

3[(5-bromo-2-thienyl)propenylidene]2,4(3H,5H)-furandione

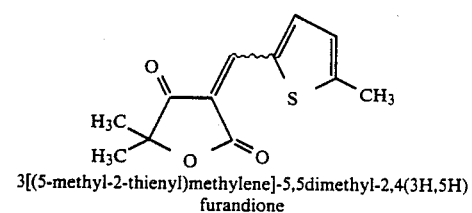

3[(5-methyl-2-thienyl)methylene]-5,5dimethyl-2,4(3H,5H) furandione

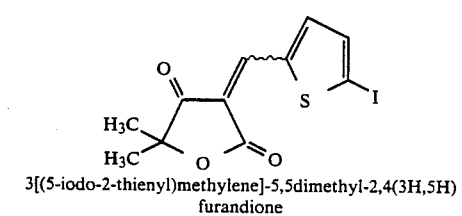

3[(5-iodo-2-thienyl)methylene]-5,5dimethyl-2,4(3H,5H) furandione

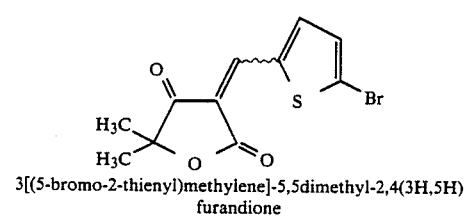

3[(5-bromo-2-thienyl)methylene]-5,5dimethyl-2,4(3H,5H) furandione

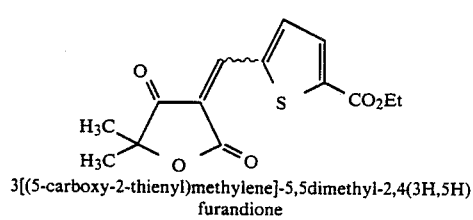

3[(5-carboxy-2-thienyl)methylene]-5,5dimethyl-2,4(3H,5H) furandione

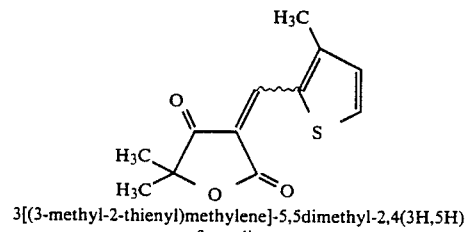

3[(3-methyl-2-thienyl)methylene]-5,5dimethyl-2,4(3H,5H) furandione

The other subclass of the furandiones used in accordance with the present invention are the 3-(arylalkylene)2,4(3H,5H) furandiones, including, for example, those represented by the following general formula:

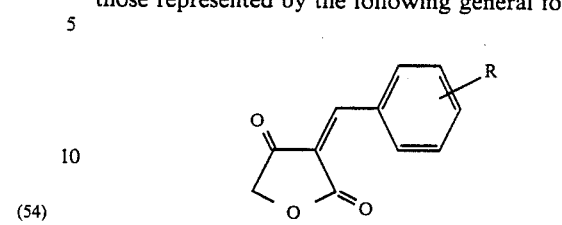

where R represents hydrogen, N,N-dimethyl amine and chlorine. For example, the 3-(arylalkylene)2,4(3H,5H) furandiones include 3[(3,4-dichlorophenyl)methylene]2,4(3H,5H)-furandione; 3[(2,4-dimethoxyphenyl)methylene]2,4(3H,5H)-furandione and 3[(4-N,N-dimethylamino)methylene]2,4(3H,5H) furandione, the structural formulae of which are as follows:

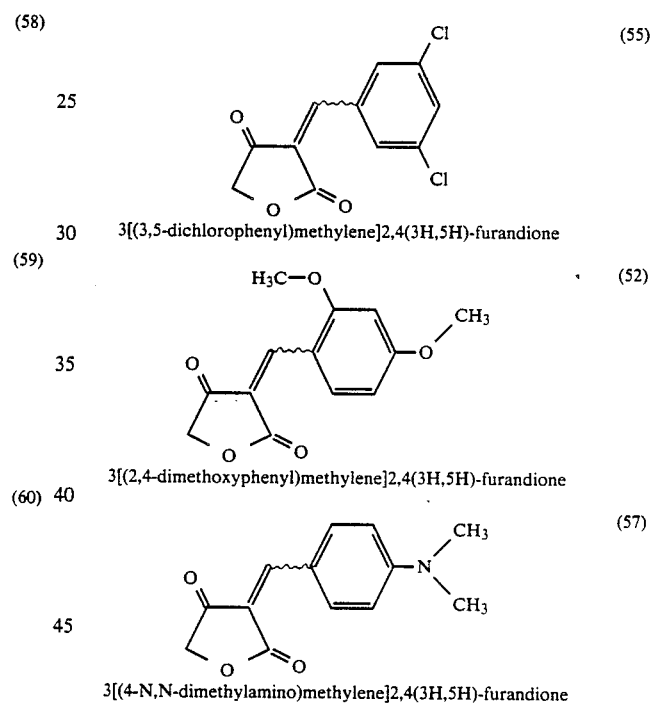

Another class of compounds, the 3-(heteroarylalkylene)2,4(3H,5H)pyrrolidene diones, included in the present invention are generally represented, for example, by those of the following formula:

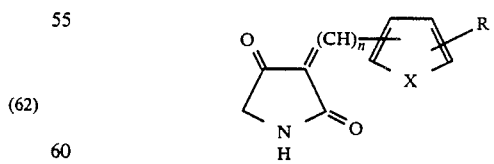

where R represents hydrogen, carboxyl or the ethyl ester thereof, methoxy, N-piperidenyl, morpholino, alkyls containing one to three carbon atoms such as methyl, ethyl, and propyl, or halogens such as chlorine, fluorine, bromine, and iodine; and X represents oxygen, sulphur or an amine; and n is 1 or 3.

For example, the 3-(heteroarylalkylene)-2,4-(3H,5H) pyrrolidene diones include

3-[(5-methyl-2-thienyl)methylene]-2,4(3H,5H)-pyrrolidene dione;

3-[(5-bromo-2-thienyl)methylene]2,4(3H,5H)-pyrrolidene dione;

3-[(5-ethoxycarbonyl-2-thienyl)methylene]2,4(3H,5H)-pyrrolidene dione;

3-[(3-methyl-2-thienyl)methylene]2,4(3H,5H)-pyrrolidene dione;

3-[(5-methyl-2-thienyl)propenylidene)2,4(3H,5H)-pyrrolidene dione, the structural formulas of which are as follows:

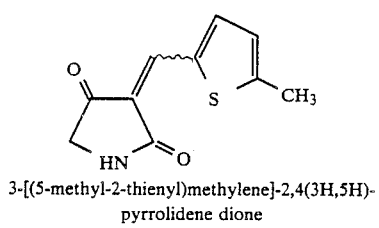

(63)

3-[(5-methyl-2-thienyl)methylene]-2,4(3H,5H)-pyrrolidene dione

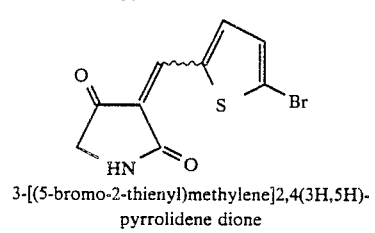

(64)

3-[(5-bromo-2-thienyl)methylene]2,4(3H,5H)-pyrrolidene dione

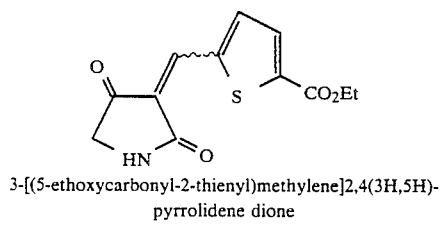

(65)

3-[(5-ethoxycarbonyl-2-thienyl)methylene]2,4(3H,5H)-pyrrolidene dione

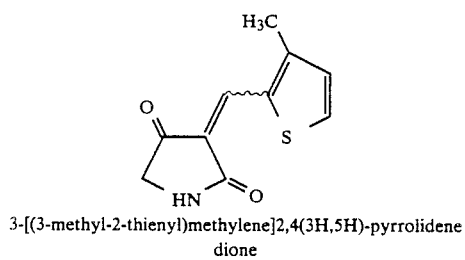

(66)

3-[(3-methyl-2-thienyl)methylene]2,4(3H,5H)-pyrrolidene dione

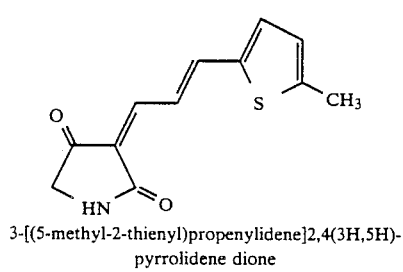

(67)

3-[(5-methyl-2-thienyl)propenylidene]2,4(3H,5H)-pyrrolidene dione

Another class of compounds used with the present invention include the 3-(heteroarylalkylene)2,4-(3H,5H)-thiophenediones, examples of which are generally represented by the following formula:

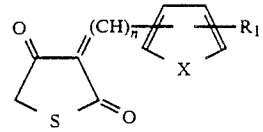

where $R_1$ represents hydrogen, carboxyl or the ethyl ester thereof, methoxy, N-piperidenyl, morpholino, alkyls containing one to three carbon atoms such as methyl, ethyl, and propyl, or halogens such as chlorine, fluorine, bromine, and iodine; and X represents oxygen, sulphur, or an amine; and n is 1 or 3.

For example, the 3-(heteroarylalkylene)-2,4-(3H,5H)-thiophenediones include

3[(5-methyl-2-thienyl)methylene]-2,4(3H,5H)-thiophenedione and

3-[(5-bromo-2-thienyl)methylene]-2,4(3H,5H)-thiophenedione, the structural formulas of which are as follows:

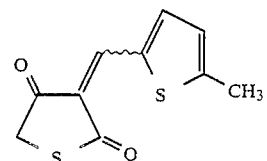

(69)

3[(5-methyl-2-thienyl)methylene]-2,4(3H,5H)-thiophenedione

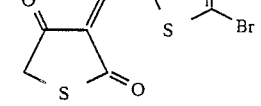

(70)

3-[(5-bromo-2-thienyl)methylene]-2,4(3H,5H)-thiophenedione

The following examples demonstrate the effectiveness of the class of 3-(heteroarylalkylene)-2, 4 (3H, 5H) furandiones against cancerous tumor cells, both in vitro and in vivo.

EXAMPLE 1

The in vitro Human Tumor Stem Cell Assay procedure described as follows has several advantages for testing the effectiveness of chemotherapy drugs such as the 3-(heteroarylalkylene)-2,4(3H,5H)-furandiones. The first advantage is that fresh tumor cells from a variety of tumor types were used rather than a small number of cell lines which have undergone severe selection pressures as they are passed in vitro. The second advantage is that only the anchorage-independent tumor cells will form colonies in soft agar so that any non-malignant cells present in the sample will not form colonies. Perhaps the most important advantage, however, is the emphasis on cells which have the ability to form colonies. These cells, which are generally called stem cells, usually comprise only a small percentage of all tumor cells. They are thought to be the most important cells for growth and distant spread of a tumor. In particular, these cells have the potential to leave the primary tumor and form new tumors at distant sites (called metastases). It is the effectiveness against these very important stem cells that the Human Tumor Stem Cell Assay measures.

One of the 3-(heteroarylalkylene)-2,4(3H,5H)-furandione compounds, 3-[(5-methyl-2-thienyl) methylene]-

2,4(3H,5H)-furandione was evaluated against a series of 10 human tumors in the in vitro Human Tumor Cell Assay, along with conventional and standard chemotherapy agents.

In the procedure, a single cell suspension was prepared from tumors excised from patients during therapeutic or diagnostic surgical procedures. The human tumor cells were exposed to known anticancer drugs or to [(5-methyl-2-thienyl)methylene]-2,4 (3H, 5H)-furandione at a low (0.2 mcg/ml) or a high (1.0 mcg/ml) concentration for one hour. Control cultures showed that appropriate concentrations of the solvent dimethylsulfoxide (DMSO) had no effect on cancer colony growth. The suspension was washed with tissue culture medium to remove the drug.

of the compound. On the other hand, a large number like 120 means that the number of colonies is 20% greater with the compound than without.

Of the nine tumors for which the higher concentration (1.0 mcg/ml) of the furandione was used, five gave inhibition of colony growth corresponding to borderline sensitive (30–50% growth) and four gave inhibition corresponding to sensitivity (0–30% growth). Clinical drugs are normally tested at 10% of their peak plasma concentration. For the standard chemotherapy drugs shown in Table 1, the low concentration (LO) corresponds to this 10% level, and the high concentration (HI) is at 50% of the peak plasma concentration. Of the same nine tumors, only two would have been rated as sensitive or borderline sensitive to any of the other clinical drugs tested.

TABLE 1

| DRUG | H5315 BREAST | H5318 OVARY | H5319 BREAST | H5322 STOMACH | H5325 SARCOMA | H5330 THYMUS | H5331 OVARY | H5337 COLON | H5340 ** | H5349 BREAST |
|---|---|---|---|---|---|---|---|---|---|---|
| ADR-HI | | 60 | 100 | 65 | 11 | 98 | 105 | | | |
| ADR-LO | 75 | 76 | | 55 | 22 | | | | | 82 |
| VBL-HI | | 60 | 6 | 35 | 8 | | 45 | 67 | 44 | 65 |
| VBL-LO | 50 | 39 | 5 | 40 | 9 | | 115 | 60 | 79 | 70 |
| MTC | | 90 | 72 | 69 | | 90 | 102 | | | |
| MTC-LO | 59 | | | | | | | | | |
| BCNU-HI | | 93 | 122 | | | 74 | 111 | 88 | | |
| BCNU-LO | 108 | | | | | | | | | |
| CPDD-HI | | 38 | | 56 | | 75 | 69 | 41 | 125 | 54 |
| CPDD-LO | | 109 | | 63 | 62 | | 87 | 98 | | 48 |
| HXM-HI | | 102 | | | | | 84 | | | |
| MPL-HI | | | 85 | 61 | 12 | 92 | 76 | 58 | | 65 |
| MPL-LO | | | | 54 | | 31 | | 76 | | 63 |
| 5FU-HI | | 111 | | 79 | 83 | | 51 | | | 117 |
| 5FU-LO | | | | | | | 94 | 62 | | |
| 6TG-HI | | | | 122 | 69 | | | | 50 | |
| 6TG-LO | | | | | | | | | 75 | |
| DTIC-HI | | | | | | 59 | | | | |
| DTIC-LO | | | | | | 91 | | | | |
| VP16-HI | | | | | | 77 | | | | |
| BLM-HI | | | | | | 59 | | | 71 | |
| BLM-LO | | | | | | 67 | | | | |
| VCR-HI | | | | | | | | | 113 | |
| ACT-HI | | | | | 22 | | | | | |
| ACT-LO | | | | | 6 | | | | | |
| AZO-HI | | | | | | | | | 107 | |
| COMBO1 | | 82 | | | | | | | | |
| COMBO2 | | 88 | | | | | 69 | | | |
| TEST-HI* | | 29 | 6 | 36 | 22 | 38 | 48 | 36 | 50 | 9 |
| TEST-LO | (62) | 210 | 68 | 44 | 79 | 64 | 58 | 62 | 82 | |

HXM: HEXAMETHYLMELAMINE
ADR: ADRIAMYCIN
MTC: MITOMYCIN C
CPDD: CISPLATIN
AZQ: AZIRIDIMYLBENYOQUINONE
BCNU: BISCHLORETHYLNITROSOUREA
VBL: VINBLASTINE
VCR: VINCRISTINE
MPL: MELPHALAN
COMBO1: MPL.ADR.CPDD
5FU: 5-FLUORACIL
6TG: 6-THIOQUANINE
DTIC: DACARBAZINE
ACT: ACTINOMYCEN D
COMBO2: 5FU.MPL

The suspension was then cultured in a double soft agar suspension. Control cells which had been treated identically, except for exposure to the drugs, were also cultured. After one to two weeks, both the tumor cells and the control cells formed colonies in the soft agar which were enumerated under a microscope. The number of colonies grown from the drug-treated cells was compared to the number of colonies grown from the control cells, and the percentage growth after exposure to the drug was calculated.

The results are illustrated in Table 1, wherein the various numbers indicate the percentage of growth. For example, a small number like 6 means that the number of colonies is only 6% of the number without addition There is considerable literature indicating that the Human Tumor Stem Cell Assay can predict the effectiveness of a particular chemotherapy agent. Studies of multiple tumors treated with many different drugs indicate that if a tumor is resistant to a drug in vitro there is greater than 90% probability that it will be resistant in vivo. Moreover, if the tumor is sensitive in vitro, there is a 60–70% probability it will be sensitive in vivo. See *In Vitro Assay For Sensitivity to Anticancer Drugs*, by Sydney E. Salmon, published in Hospital Practice, June 15, 1985, pp. 133–148; and *Association Between Human*

*Tumor Colony—Forming Assay Results and Response of an Individual patient's Tumor to Chemotherapy,* by Daniel D. Von Hoff, et al., published in The American Journal of Medicine, May 1981, pp. 1027–1032.

In summary, it is apparent from Table 1 that the tested furandione is extremely active against a wide variety of human solid tumors in vitro with a one hour exposure at a concentration of 1 mcg/ml. Therefore, by analogy with other chemotherapy drugs, this compound should be effective in vivo at a peak plasma concentration of 10 mcg/ml.

EXAMPLE 2

Toxicology Testing

The purpose of this example was to determine approximate toxicity of the compound 3[(5-methyl-2-thienyl) methylene]-2,4(3H,5H)-furandione in healthy mice. The in vivo concentrations employed in the example were selected by using the in vitro results in the Human Tumor Stem Cell Assay as a guide. The compound was given to the mice by means of intra-peritoneal injection. In addition to a control group which was injected with the appropriate carrier solution without drug, three test groups with calculated plasma concentrations of 1, 10 and 100 mcg/ml (low, medium and high concentrations) were prepared. Based upon the results from Table 1, the three test groups represent low, medium and high concentrations of drug dosages. The highest concentration of 100 mcg/ml is about 10 times the predicted effective dose (in vivo) of tumoricidal activity. Each group contained eight animals. Blood was extracted from four animals in each group two days after the intraperitoneal injection and routine hematology (i.e., a hemoglobin concentration, a white blood cell count, and a neutrophil count) procedures were performed.

Half of the animals in each group were sacrificed after one week (Day 7), and the remaining animals in each group were sacrificed after two weeks (Day 14). Routine hematology was performed at the time of sacrifice. The results of hematology testing including Day 2, Day 7, and Day 14 are shown in Table 2.

obtaining a blood sample from the orbital sinus. Accordingly, it appears that the LD50 of this compound is greater than the largest dose (100 mcg/ml) used in the study. There were no significant decreases in hemoglobin levels in any of the test group during the 14-day test period, and an examination of the blood smears indicate that the platelet count was not significantly decreased. Although the total white blood cell count slightly decreased from Day 2 to Day 7, the count increased in all groups from Day 7 to Day 14 to the extent that the total count increased from Day 2 to Day 14. There was a significant decrease in the absolute neutrophil count after one week, indicating suppression of bone marrow by the test compound. At this time, the control group averaged 2,283 neutrophils per microliter (SD=755), the 1 mcg/ml group averaged 1,731 neutrophils per microliter (SD=942), the 10 mcg/ml group averaged 1,009 neutrophils per microliter (SD=492), and the 100 mcg/ml group averaged 1,167 neutrophils per microliter (SD=622). There is no significant difference between the control and the low concentration group. However, there is a significant difference between the control group and the medium and high drug concentration groups. The statistical probability (P) that the significant difference occurred by chance alone for the medium concentration group was determined to be less than 5% ($p<0.05$). The probability that the significant difference occurred by chance alone for the high concentration group was determined to be between 5% and 10% ($0.05 < P < 0.1$). Therefore, there is some myelosuppression in vivo at the drug level predicted by the in vitro assay.

As previously stated, half of the animals in each group were sacrificed after one week (Day 7), and the remaining animals were sacrificed after two weeks (Day 14). Full pathological evaluations were conducted on each animal to determine the effect of the drug on the organs, breathing passages, bones, and brain of the animals. The results from the pathological evaluations are set forth below in Table 3. The first 8 tested animals represent the control group, animals 9–16 prepresent

TABLE 2

HEMATOLOGICAL VALUES OF MICE INJECTED WITH 3[[5-methyl-2-thienyl]methylene] 2, 4 (3H, 5H) FURANDIONE

| | Hemoglobin (g/100 ml) | | | WBC, Cells/ul | | | Absolute Neutrophils, cells/ul | | |
|---|---|---|---|---|---|---|---|---|---|
| | Day 2* | Day 7* | Day 14* | Day 2* | Day 7* | Day 14* | Day 2* | Day 7* | Day 14* |
| Control | 15.2 | 14.25 | 13.5** | 7012 | 5912 | 9450** | 2600 | 2283 | 4084** |
| Low Drug | 13.7 | 14.25 | 13.6 | 7000 | 6562 | 9675 | 2869 | 1731 | 2183*** |
| Medium Drug | 13.6 | 13.9 | 13.6 | 7787 | 5812 | 8700 | 3946 | 1009 | 1256*** |
| High Drug | 13.2 | 13.6 | 13.9 | 9594 | 5775 | 12,175 | 5224 | 1167 | 2025 |

Except as noted, all values represent the average of five animals.
*Days After Injection
**Two animals in this group.
***Three animals in this group.

During the testing period there were no deaths due to the tested furandione compound. The only deaths prior to sacrifice were two control animals which died while obtaining the low concentration group, animals 17–24 represent the medium concentration group, and animals 25-32 represent the high concentration control group.

TABLE 3

| | Animal No. | | | | | | | | | | | | | | | | |
|---|---|---|---|---|---|---|---|---|---|---|---|---|---|---|---|---|---|
| Organ, etc. | 1 | 2 | 3 | 4 | 5 | 6 | 7 | 8 | 9 | 10 | 11 | 12 | 13 | 14 | 15 | 16 | 17 |
| Trachea | X | X | X | N | N | X | X | N | N | X | X | N | N | X | N | N | N |
| Lungs | X | X | X | X | X | 2a | X | 3a | 2a | X | X | X | X | X | 1b | 1b | X |
| Heart | X | X | X | X | X | X | X | X | X | X | X | X | X | X | X | X | X |
| Stomach | X | X | X | X | X | X | X | X | X | X | X | X | X | X | X | X | X |
| Duodenum | X | X | X | X | X | X | X | X | X | X | X | X | X | X | X | X | X |
| Jejunum | X | X | X | X | X | X | X | X | X | X | X | X | X | X | X | X | X |
| Ileum | X | X | X | X | X | X | X | X | X | X | X | X | X | X | X | X | X |

TABLE 3-continued

| Organ, etc. | | | | | | | | | | | | | | | | |
|---|---|---|---|---|---|---|---|---|---|---|---|---|---|---|---|---|
| Cecum | X | X | X | X | X | X | X | X | X | X | X | X | X | X | X | X |
| Pancreas | X | X | X | X | X | X | X | X | X | X | X | X | X | X | X | X |
| Liver | X | X | X | X | X | X | X | X | X | X | X | X | X | 1 | X | X |
| Kidney (R) | X | X | X | X | X | X | X | X | 2 | X | X | X | X | X | X | X |
| Kidney (L) | X | X | X | X | X | X | X | X | 2 | X | X | X | X | X | X | X |
| Urinary Bladder | X | X | X | X | X | X | X | X | X | X | X | X | X | X | X | X |
| Spleen | X | X | X | X | X | X | X | X | X | X | X | X | X | X | X | X |
| Bone Marrow Sternum | X | X | X | X | X | X | X | X | X | X | X | X | X | X | X | X |
| Cerebrum | X | X | X | X | X | X | X | X | X | X | X | X | X | X | X | X |
| Cerebellum | X | X | X | X | X | X | X | X | X | X | X | X | X | X | X | X |
| Medulla | X | X | X | X | X | X | X | X | X | X | X | X | X | X | X | X |

| Organ, etc. | Animal No. | | | | | | | | | | | | | | |
|---|---|---|---|---|---|---|---|---|---|---|---|---|---|---|---|
| | 18 | 19 | 20 | 21 | 22 | 23 | 24 | 25 | 26 | 27 | 28 | 29 | 30 | 31 | 32 |
| Trachea | N | N | I | I | N | N | X | N | N | N | N | X | N | N | N |
| Lungs | X | X | X | X | X | X | X | X | X | X | 3a | X | X | X | X |
| Heart | X | X | X | X | X | X | XA | XA | X | X | X | X | X | X | X |
| Stomach | X | X | X | X | X | X | X | X | X | X | X | X | X | X | X |
| Duodenum | X | X | X | X | X | X | X | X | X | X | X | X | X | X | X |
| Jejunum | X | X | X | X | X | X | X | X | X | X | X | X | X | X | X |
| Ileum | X | X | X | X | X | X | X | X | X | X | X | X | X | X | X |
| Cecum | X | X | X | X | X | X | X | X | X | X | X | X | X | X | X |
| Pancreas | X | X | X | X | X | X | X | X | X | X | X | X | X | X | X |
| Liver | X | X | X | X | X | X | X | X | X | X | X | X | X | X | X |
| Kidney (R) | X | X | X | X | X | X | X | X | X | X | X | X | X | X | X |
| Kidney (L) | X | X | X | X | X | X | X | X | X | X | X | X | X | X | X |
| Urinary Bladder | X | X | X | X | X | X | X | X | X | X | X | I | X | X | X |
| Spleen | X | X | X | X | X | X | XA | X | X | X | X | X | X | X | X |
| Bone Marrow Sternum | X | X | X | X | X | X | X | X | X | X | X | X | X | X | X |
| Cerebrum | X | X | X | X | X | X | XA | X | X | X | X | X | X | X | X |
| Cerebellum | X | X | X | X | X | X | XA | X | X | X | X | X | X | X | X |
| Medulla | X | X | X | X | X | X | XA | X | X | X | X | X | X | X | X |

X = Not Remarkable
N = No Section
I = Incomplete Section
A = Artifact of Tissue Election or Processing
1 = Minimal
2 = Slight
3 = Moderate
4 = Moderately Severe—High
Abnormalities were confined to the following:
Lung (a) focal alveolar consolidation by purulent exudates (b) few scattered foam-cell aggregates
Kidney - focal interstitial aggregates of mononuclear epithelioid plasma cytoid cells
Liver - focal extramedullary hematopoiesis The data indicate that the organs, bone, brain, etc., were not remarkably altered within the testing period (7 days or 14 days) by the drug 3((5-methyl-2thienYl)methylene) 2,4 (3H, 5H) furandione. In particular, even high concentrations of the drug do not appear to affect any of the organs, bone, etc. of the test animals to any lesser or greater degree than the low concentration drug group or the control group.

EXAMPLE 3

The purpose of this example was to demonstrate that other members of the family of 3-(heteroarylalkylene) 2,4(3H,5H)-furandiones are effective against human cancer tumor cells (i.e., inhibit or kill human cancer tumor cells).

In this example, 1 mcg/ml of 3[[5-methyl-2-thienyl]methylene]2, 4 (3H, 5H) furandione was compared to 1 mcg/ml of 3[[3-methyl-2-thienyl]methylene]2, 4 (3H, 5H) furandione.

A conventionally available cell line (K562) derived from human chronic granulocytic leukemia was employed in an in vitro procedure. The leukemia cell line was cultured in a suspension of RPMI 1640 plus 10% fetal calf serum. All initial cell concentrations for the cultures were 0.65 times $10^5$ cells/ml. Four separate suspension cultures were employed with the first suspension culture having no additions. The second suspension culture included 100 microliters of the solvent DMSO per 10 ml of culture (control). The third culture contained 1 ug/ml of 3[[5-methyl-2 thienyl]methylene]-2, 4 (3H, 5H) furandione and the fourth culture contained 1 ug/ml of 3[[3-methyl-2-thienyl]methylene]-2, 4 (3H, 5H) furandione. The cell concentration of each of the four cultures was determined. After three days and again after five days. The results are set forth in Table 4 below.

TABLE 4

| | 3 Days Cell Conc. | 5 Days Cell Conc. |
|---|---|---|
| Standard: | $3.1 \times 10^5$/ml | $4.1 \times 10^5$/ml |
| DMSO Control: | $2.8 \times 10^5$/ml | $5.1 \times 10^5$/ml |
| 5 methyl* | $0.7 \times 10^5$/ml | $0.5 \times 10^5$/ml |
| 3 methyl** | $0.5 \times 10^5$/ml | $1.5 \times 10^5$/ml |

*3[[5-methyl-2-thienyl]methylene]-2,4(3H,5H)-furandione.
**3[[3-methyl-2-thienyl]methylene]-2,4(3H,5H)-furandione.

The third example demonstrates that, after three days, the in vitro exposure of the compound to leukemia cells is effective to about the same degree. Additionally, after three days, the cell concentration of the standard and DMSO control is about equal. Both compounds demonstrate a marked decrease in the cell concentration of the leukemia culture. After five days, the 3-methyl isomer had a slightly higher cell concentration than the 5-methyl analog. The compound 3[[5-methyl-2-thienyl]methylene]2,4 (3H, 5H) furandione is very effective against the leukemia culture as demonstrated by the remarkable decrease in cell concentration. The compound 3[[3-methyl-2-thienylmethylene]2,4 (3H, 5H) furandione also shows a decrease in the leukemia cell concentration culture, but the decrease is not as great as with the other compound. Nevertheless, these tests indicate that both compounds are excellent at inhibiting leukemia cell growth in vitro.

Thus, it is apparent that there has been provided, in accordance with the invention, a method that fully satisfies the objects, aims and advantages set forth above. While the invention has been described in conjunction with specific embodiments thereof, it is evident that many alternatives, modifications, and variations will be apparent to those skilled in the art in light of the foregoing description. Accordingly, the invention is intended to embrace all such alternatives, modifications and variations as fall within the spirit and scope of the invention.

EXAMPLE 4

The purpose of this example was to demonstrate that other members of the family comprising 3-(heteroarylalkylene)- and 3-(arylalkylene)-2,4(3H,5H)-furandiones and 3-(heteroarylalkylene)2,4(3H,5H)-pyrrolidene diones and -thiophenediones are effective against Human Cancer Tumor Cells (i.e., inhibit or kill Human Cancer Tumor Cells).

In this example, aliquots of 1.0, 5.0 and 10.0 mcg/ml of each of the family compounds was prepared and assayed against KS62 strain stem-cell human leukemia cells in an in vitro procedure as done in Example 3 above.

The results of these assays are shown in Table 5. The results indicate that a great majority of this representative sample of family member compounds used in accordance with the present invention inhibited the growth of human leukemia cells even at concentrations as low as 1.0 mcg/ml. Compounds are referenced by a number corresponding to their structure disclosed above (e.g., Compound Number 4 is 3[(5-methyl-2-thienyl)methylene]2,4(3H,5H)-furandione).

TABLE 5

| Compound Number | % Inhibition at: | | |
|---|---|---|---|
| | 1.0 mcg/ml | 5.0 mcg/ml | 10.0 mcg/ml |
| 4 | 32% | 97% | 100% |
| 48 | 0% | 0% | 98% |
| 49 | 0% | 0% | 98% |
| 45 | 0% | 0% | 100% |
| 50 | 0% | 0% | 0% |
| 51 | 37% | 100% | 100% |
| 52 | 8% | 38% | 95% |
| 53 | 0% | 71% | 99% |
| 54 | 27% | 99% | 100% |
| 55 | 0% | 0% | 0% |
| 56 | 0% | 0% | 0% |
| 57 | 17% | 94% | 96% |
| 58 | 51% | 97% | 100% |
| 59 | 1% | 37% | 94% |
| 60 | 0% | 96% | 100% |
| 61 | 0% | 18% | 42% |
| 62 | 6% | 99% | 100% |
| 63 | 0% | 0% | 0% |
| 64 | 0% | 0% | 0% |
| 65 | 7% | 32% | 75% |
| 66 | 0% | 15% | 54% |
| 67 | 0% | 0% | 94% |
| 68 | 0% | 0% | 0% |
| 69 | 13% | 41% | 100% |
| 70 | 22% | 30% | 54% |

The following are examples of synthetic procedures for some of the compounds which are the subject of the present invention.

EXAMPLE A

Preparation of 3[(5-methyl-2-thienyl)-methylene]-2,4(3H,5H-furandione 0.72 gm of finely powdered tetronic acid (FW=100, 7.2 mmole) was added to 2.18 gm of 5-methyl-2-thiophenecarboxaldehyde (FW=126, 71.3 mmole) in a 25 mL roundbottom flask with a magnetic stirrer. 1.0 mL of concentrated HCl was added and the solution stirred until it solidified (i.e., approximately 5 minutes). 25 mL of ether and 20 mL of water were added, the sludge swirled and the solid yellow compound collected on a buchner funnel, washed with ether, water and ether again. The crystals were dissolved in hot $CHCl_3$ and passed through a silica plug. After removal of the solvent the compound was recrystallized from ethyl acetate/ligroin. The yield was 0.61 gm (41%), molecular formula: $C_{10}H_8O_3S$. NMR results were as follows: 1 HNMR (d6DMSO ($H_2O$)/TMS) $\delta 2.64$ (3H, bs); 4.68 (2H, d, 6 Hz); 7.13 (1H,m); 8.13 (2H, m).

EXAMPLE B

Preparation of 3-[(5-iodo-2-thienyl)-methylene]-2.4(3H,5H)-furandione 0.59 gm of tetronic acid (FW=100, 0.056 mole) and 3.65 gm of 5-iodo-2-thiophenecarboxaldehyde (FW=238, 15.3 mmole) were added to a 25 mL roundbottom flask and 2.5 mL of THF were added and the solution was stirred for five minutes. The sludge was allowed to react for 30 minutes, occasionally helping the stirring with a glass rod. The precipitate was then treated with 10 mL of ether and 10 mL of water and swirled. The yellow crystals were then collected on a buchner funnel, washing them with ether, water and ether again. The excess 5-iodo-2-thiophenecarboxaldehyde was then recovered by extracting to aqueous layer with ether and resublimed. The crude adduct was dissolved in hot $CHCl_3$ (approximately 250 mL) and passed through a silica plug (approximately 5 cm). The crystals obtained after solvent evaporation were recrystallized from ethyl acetate/igroin and the yield was 0.85 gm (46%). The material melted at 211°–212° C. (dec.) $C_9H_6IO_3S$: %C 33.77; %H 1.57; found %C 33.53; %H 1.83 NMR results: 1HNMR (d6DMSO,($H_2O$)/TMS) $\delta$ 4.69 (2H, d, 4.8 Hz); 7.53 (1H, m); 8.08 (1H, m).

EXAMPLE C

Preparation of 3-[(5-bromo-2-thienyl)-methylene]-2,4(3H,5H-furandione 0.60 gm of tetronic acid (FW=100, 6.0 mmole) and 1.8 mmole of 5-bromo-2-thiophenecarboxaldehyde (FW=152, 3 equivalents) were stirred as previously and 1 mL of concentrated HCl was added. The mixture solidified after 5 minutes. The workup was the same as in Example A. The yield was 0.78 gm (56%) M. p. 207+–208°. $C_9H_5BrO_3S$: calculated %C 39.58; %H 1.85; found %C 39.74; %h 2.09.

EXAMPLE D

Preparation of 3-[(5-ethoxycarbonyl-2-thienyl)-methylene]-2,4(3H,5H)-furandione 0.494 gm of tetronic acid (FW=100, 4.94 mmole) and 2.00 gm of ethyl-5-carboxy-2-thiophenecarboxaldehyde (FW=184, 10.9 mole) in 2mL of THF and 10 mL of concentrated HCl was reacted as before by applying heat and efficient stirring. The total reaction time was 10 minutes. Workup and recrystallization from methanol gave 0.827 gm (63%) of the product. M. p. 204°–205.5° C. $C_{12}H_{10}O_4S$: %C 564.13; %H 3.79; found %C 53.93; %H 4.00. NMR results: 1HNMR (d6DMSO (H$_2$)/TMS $\delta$1.39 (3H, t, 7HZ); 4.39 (2H, q, 7Hz); 7.83 (1H, d, 4Hz); 8.21 (2H, m).

EXAMPLE E

Preparation of 3-[(5-carboxy-2-thienyl)-methylene]-2,4(3H,5H)-furandione

As before, 0.571 gm of tetronic acid (FW=100, 5.7 mmole) was reacted with 2.2 equiv. or 1.96 gm of 5-carboxy-2-thiophenecarboxaldehyde with 6 mL of THF and 10.5 mL of conc. HCl and applied heat. A greenish precipitate formed immediately. Stirring was continued for 10 minutes. Workup and recrystallization from methanol gave 0.91 gm (67%) of the product having a M. p. of approximately 255°–268° C. and a molecular formula of $C_{10}H_6O_5S$: calculated %C 50.42; %H 2.54; found %c 50.22; %H 2.75.

EXAMPLE F

Preparation of 3-[(3-methyl-2-thienyl)methylene]-2.4(3H.5H)-furandione 1.00 gm of tetronic acid (FW=100, 10mmole) was added to a stirring solution of 3.78 gm of 3-methyl-2-thiophenecarboxaldehyde (FW=126, 30 mmole) together with 1 mL conc. Hcl. The mixture was stirred for 40 minutes after which all had solidified. The residue was dissolved in CHCl$_3$ and washed with water, dried with HgSO$_4$, filtered and put through a silica plug with CHCl$_3$. The yellow crystals had a melting point of 164°–166° C. (lit. 164–165). The yield was 42%. All other spectral data corresponded with the published ones. $C_{10}H_8O_3S$: %C 57.69; %H 3.87; found %C 57.81; %H 3.82. NMR results: 1HNMR (d6DMSO(H$_2$0)/TMS) $\delta$ 2.56 (3H, s); 4.71 (2H, d, 7 Hz); 7.28 (1H, m); 8.01 (1H, m); 8.27 (1H, m).

EXAMPLE G

Preparation of 3-[(2,4-dimethoxy-1-phenyl)methylene]-2,4(3H,5H)-furandione 6.0 mmole of tetronic acid and 15.0 mmole of 2,4-dimethoxybenzaldehyde were mixed with 30 mL of absolute EtOH and 2 drops of conc. HCl. The mixture was stirred for 2.5 hrs. at 50° C. after which the ethanol was removed in vacuo. Water and ether were added and the organic phase was washed with water. After removing the solvent, the yellow material was dissolved in CHCl$_3$ and recrystallized from absolute ethanol to give fine yellow needles. The yield of the product was 53% with a M. p. of about 172°–174.5° C. The formula of the product is $C_{13}H_{12}O_6$ calculated: %C 62.90; %H 4.87; found %C 63.05; %H 4.98. NMR results: 1HNMR (CDCl$_3$/TMS) $\delta$ 6 3.93 (6H, s); 4.59 (2H, d, 9Hz); 6.41 (1H, d, 3Hz); 6.62 (1H, m); 8.57 (1H, d 3 Hz); 9.30 (1H, d, 9Hz).

EXAMPLE H

Preparation of 3-[(5-methyl-2-thienyl)propylenediene)-2,4(3H,5H)-furandione 2.7 mmole of tetronic acid and 3.3 mmole of -5-methyl-2-thiophene carboxaldehyde in 5 mL of absolute EtOH with 3 dps. of conc. HCl were stirred magnetically. After the tetronic acid had dissolved, the mixture was cooled and ether and water were added and the mixture was filtered. The crystals were dissolved in CHCl$_3$ and put on a column. The product was eluted with 20% MeOH/CHCl$_3$. The product was recrystallized from abs. EtOH. The yield was 38%. The melting point was 199°–201° C. $C_{12}H_{10}O_3$: calculated %C 61.54; %H 4.30; found %C 61.70; %H 4.70. NMR results: 1HNMR (Unisol (H$_2$O)/TMS) $\delta$2.57 (3H, s); 4.57 (2H, d, 3 Hz); 6.87 (3H, m); 7.36 (1H, d, 4Hz); 7.70 (1H, m).

EXAMPLE I

Preparation of 3-(5-bromo-2-thienyl)propylenediene]-2,4(3H.5H)-furandione 1.6 mmole of tetronic acid and 2.3 mmole of 5-bromo-2-thiophene carboxaldehyde and 5 mL of abs. EtOH with 2 dps of conc. HCl were stirred at 50°–60° C. for 4 hours, during which time a red precipitate formed. Water was added, the precipitate filtered and put through a column with CHCl$_3$. The product was recrystallized from isopropyl alcohol. The yield was 61%. The crystals melted at 204°–206° C. (dec.). Molecular formula: $C_{11}H_{17}SO_3Br$: calculated %C 44.16; %H 2.36; found %C 44.01; %H 2.39. NMR results: 1HNMR (d6DMSO (H$_2$O)/TMS) $\delta$4.63 (2H, d, 6Hz); 7.35 (2H, dd, 4Hz); 7.81 (3H, m).

EXAMPLE J

Preparation of 3-[(3,4-dichloro-1-phenyl)methylene]-2,4(3H,5H)-furandione 1.7 mmole of tetronic acid and 2.9 mmole of 3,5-dichlorobenzaldehyde were mixed and refluxed in 4 mL of abs. EtOH with one drop of conc. HCl for one hour under nitrogen. After the usual workup the product was chromatographed using CHCl$_3$ as the eluant. The yellow crystals were recrystallized from EtOAc/ligroin. The yield was 28%. The m. p. was 182°–183.5° C. $C_{11}H_6O_3CL_2$: calculated %C 51.39; %H 2.35; found %C 51.58; %H 2.33. NMR results: 1 HNMR (CDCl$_3$/TMS) $\delta$ 4.70 (2H, d, 3Hz); 7.60 (1H, m); 7.83 (1H, s), 8.32 (2H, s).

EXAMPLE K

Preparation of 3-(5-N-piperidyl-2-thienyl)methylene]-2,4(3H,5H)-furandione 1.0 mmole of tetronic acid and 1.3 mmole of 5-N-piperidyl-2-thiophene carboxaldehyde were mixed with 5 mL of isopropanol (methanol, or ethanol do not work here) and 0.5 mL of pyridine. The mixture was refluxed for 45 minutes. After cooling and column chromatography using CHCl$_3$ as the eluant, 10% of purple red crystals, which oxidize very easily in the presence of air, were obtained which melted at 195°–197° C. Molecular formula: $C_{14}H_{15}NO_3S$: calculated %C 60.64; %H 5.45; found %C 60.46; %H 5.60. NMR results: 1HNMR (CDCL$_3$/TMS) δ 1.77 (6H, m); 6.62 (4H, m); 6.34 (1H, d, 6Hz); 7.59 (2H, m).

EXAMPLE L

Preparation of 3-[(4-dimethylamine-1-phenyl)methylene1-2,4(3H.5H) furandione.

The synthesis of this compound was carried out as described in reference lb with identical results.

EXAMPLE M

Preparation of 3-[(5-methyl-2-thienyl)methylene]-5,5-dimethyl-2.4(3H furandione 7.8 mmole of pulverized 5,5-dimethyltetronic acid and 2.34 mmole of 5-methyl-2-thiophenecarboxaldehyde with four drops of conc. HCl were kept for 12 hours at 40° C. (+or −10° C.). Ether and water were added to the solid mass and the mixture was filtered. The solid was chromatographed with CHCl$_3$. Recrystallization was accomplished by adding absolute EtOH and boiling off the CHCl$_3$ and letting the mixture cool. The product yield was 61%, with a M. p. of about 160.5°–161.0° C. Molecular formula: $C_{12}H_{12}O_3S$: calculated %C 60.99; %H 5.12 found %C 60.92; %H 5.21. NMR results: 1HNMR (CHCl$_3$/TMS) δ 1.54 (6H, s); 22.68 (3H, s); 7.02 (1H, m), 7.99 (2H, m).

EXAMPLE N

Preparation of 3-[(5-iodo-2-thienyl)methylene]-5.5-dimethyl-2,4 (3H)furandione 2.71 mmole of 5,5-dimethyltetronic acid and 6.3 mmole of 5-iodo-2-thiophenecarboxaldehyde were refluxed gently with 10 mL of abs. EtOH and three drops of conc. HCl for 15 minutes. Chromatography with CHCl$_3$ gave 0.3 gm (42%) of yellow crystals which melted at 182°–184° C. Molecular formula: $C_{11}H_9IO_3S$: calculated %C 37.95; %H 2.61; found %C 37.98; %H 2.56. 1HNMR (CHCl$_3$/TMS) 6 1.52 (6H, s); 7.52 2H, m); 7.97 (1H, d, 3Hz).

EXAMPLE O

Preparation of [(5-bromo-2-thienyl)methylene-5,5-dimethyl-2,4(3H) furandione 4.6 mmole of tetronic acid and 11 mmole of 5-bromo-2-thiophene-carboxaldehyde were stirred in 5 mL of THF and 2 mL conc HCl for 5 minutes. Heating to reflux was then initiated for five minutes, after which time the THF was boiled off and the mixture was heated for 20 minutes longer at 60° C. The product was cooled and subjected to a water wash and column chromatography with an ether/ligroin (1:1) mixture. The yield was 40% after recrystallization from EtOAc. M. p. 173°–175° C. Molecular formula: $C_{11}H_9O_3SBr$: calculated %C 43.87; %H 3.01; found %C 43.93; %H 3.00 NMR results: 1HNMR (CDCl$_3$/TMS) δ 1.52 (6H, s); 7.24 (1H, d, 4Hz); 7.74 (1H, d, 4Hz); 7.93 (1H, s).

EXAMPLE P

3-(5-carboxyethyl-2-thienyl)methylene1-5.5-dimethyl1-2,4(3H)furandione 0.78 mmole of 5,5-dimethyltetronic acid and 2.3 mmole of 5-carboxyethyl-2-thiophenecarboxaldehyde was heated between 110°–120° C. When all had dissolved, two drops of HCl were added and stirring was continued for three hours at 80° to 90° C. The precipitate was cooled and water (5 mL) and ether (5 mL) were added and the mixture was filtered. The crude product was put through a plug with CHCl$_3$ and recrystallized from EtOH. The yield was 57% with a melting point of 176°–178° C. $C_{14}H_{14}O_5S$: calculated %C 57.13; %H 4.79; found %C 57.14; %H 4.98. NMR results: 1HNMR (d6DMSO (H$_2$O)/CHCl$_3$/TMS) δ 1.25 (9H, m); 4.40 (2H, q, 7Hz); 7.84 (1H, d, 4Hz); 8.26 (2H,bs).

EXAMPLE Q

Preparation of 3-[(5-methyl-2-thienyl)methylene]-5,5-dimethyl-2,4(3H) furandione 7.8 mmole of 5,5-dimethyltetronic acid and 23.4 mmole of 5-methyl-2-thiopenecarboxaldehyde was mixed at 90° C. and 1 mL of HCl was added with stirring for 11 minutes. After cooling water and ether were added. The ether layer was washed with water and dried with MgSO$_4$ and passed through a silica column with ether. The solvent was removed and the material was triturated with hot ligroin and recrystallized from same. The yield of the yellow product was 26% with a melting point of 127°–128° C. $C_{12}H_{12}O_3S$: calculated %C 61.01; %H 5.01; found %C 60.92; %H 5.21. NMR results: 1HNMR (d6DMSO (H$_2$O)/TMS) δ 1.44 (6H, s); 2.56 (3H, s); 7.28 (1H, m); 8.07 (1H, m); 8.34 (1H, m).

EXAMPLE R

Preparation of 3-[(5-methyl-2-thienyl)methylene]-2,4(3H.5H) pyrrolidinedione 4.2 mmole of tetramic acid and 9.2 mmole of 5-methyl-2-thiophenecarboxaldehyde was stirred with 2 mL MeOH for 2.5 hours and then heated to reflux for 1.5 minutes. The red solution was cooled and the precipitate was filtered. The very insoluble product was recrystallized several times from isopropanol with a yield of 52%. The melting point was 234°–235° C. (dec.). $C_{10}H_9NO_2KS$: calculated %C 57.97; %H 4.3; found %C 57.71; %H 4.48. NMR results: 1HNMR (d6DMSO/TMS) δ 2.58 (3H, s); 7.75 (1H, m); 7.99 (1H, m); 8.15 (1H, bs, [NH]).

EXAMPLE S

Preparation of 3-[(5-bromo-2-thienyl)methylene-2.4(3H.5H) pyrrolidinedione 4.3 mmole of tetramic acid and 5.2 mmole of 5-bromo-2-thiophenecarboxaldehyde was stirred in 10 mL of MeOH with one drop of HCl at 50°–60° C. for 24 hours. After this time the mixture was cooled and the yellow crystals were filtered away from the Yellow oil. The crude product was put through a silica plug with CHCl$_3$ and recrystallized from isopropanol. The yield of product was 72%. The m. p. was 133° C. (dec.) $C_9H_6NO_2S$: calculated %C 39.72; %H 2.22; found %C 39.78; %H 2.48. NMR results: 1HNMR (d6DMSO/TMS) δ 3.84 (2H, d, 2Hz); 7.34 (1H, m); 7.85 (2H, m); 8.46 (1H, bs).

EXAMPLE T

Preparation of -3-[(5-carboxyethyl-2-thienyl)methylene1-2,4(3H.5H) pyrrolidinedione 4.0 mmole of tetramic acid and 6.1 mmole of 5-carboxyethyl-2-thiophenecarboxaldehyde was mixed with 10 mL EtOH and 0.5 mL conc. HCl and heated to reflux for three hours. The mixture was filtered and dissolved in $CHCl_3$ and put through a silica column. The product could be eluted with 10% $MeOH/CHCl_3$. The yield was 36%; M. p. 252°–253° C. $C_{12}H_{11}NO_4S$: calculated %C 57.41; %H 5.30; found %C 55.80; %H 4.39. NMR results: 1HNMR (d6DMSO/TMS) δ 1.33 (3H, t, 7Hz); 3.87 (2H, bs); 4.39 (2H, q, 7Hz); 7.85 (2H, m); 8.12 (1H, m); 8.63 (1H, bs).

EXAMPLE U

Preparation of 3-(3-methyl-2-thienyl)methylene1-2,4(3H,5H) pyrrolidinedione 10 mmole of tetramic acid and 25 mmole of 3-methyl-2-thiophencarboxaldehyde were mixed with 5 mL of EtOH, 1 mL conc. HCl and stirred at 90° C. until all the tetramic acid had dissolved and then refluxed another five minutes. The mixture was cooled and ether was added and the precipitate was filtered. The yellow material was put through a column with $CHCl_3$ and recrystallized from EtOH. The product yield was 40%; M. p. 171°–179° C. $C_{10}H_9NO_2S$: calculated %C 57.97; %H 4.38; found %C 57.89; %H 4 62. NMR results: 1HNMR (d6DMSO(H2)/TMSO δ 2.49 (3H, s); 3.83 (2H, s); 7.18 (1H, d, 5H); 7.76 (1H, s); 8.03 (1H, m); 8.44 (1H, s).

EXAMPLE V

Preparation of 3-[(5-methyl-2-thienyl)propylenediene]-2,4(3H,5H) pyrrolidinedione 2.5 mmole of tetramic acid and 3.3 mmole of 5-methyl-2-thiophene carboxaldehyde was stirred in 5 mL MeOH and stirred at room temperature for 4 hours. The product was filtered and put through a column with $CHCl_3$ (second fraction). The product yield was 47%. The melting point was 233°–234° C. (dec.). $C_{12}H_{11}NO_2S$: calculated %C 61.80; %H 4.75; found %C 62.00; %H 4.98. NMR results: 1HNMR (Unisol $(H_2O)$/TMS) δ 2.54 (3H, bs); 3.76 (2H, bs); 6.80 (1H, m); 7.25 (3H, m); 7.92 (2H, m).

EXAMPLE W

Preparation of 3-(5-N-piperdyl-2-thienyl)methylene1-2.4(3H.5H) pyrrolidinedione 1.0 mmole of tetramic acid and 1.3 mmole of 5-N-piperidyl-2-thiophene carboxaldehyde aldehyde and 10 mL of isopropanol and 01.5 mL of HCl was refluxed for 4 hours, cooled, filtered and chromatographed with $CHCl_3$ as the eluant. The product could be obtained by eluting with $MeOH/CHCl_3$. The product yield was 43%; M. p. 216° C. (dec.). $C_{14}H_{16}N_2O_2S$: %C 60.68; %H 5.84; found %C 60.42; %H 5.94. NMR results: 1HNMR (CDCl3/TMS) δ 1.73 (6H, bs); 3.54 (4H, m); 7.82 (2H, d, 6Hz); 5.82 (1H, bs); 6.24 (1H, m); 7.65 (2H, d, 7Hz).

EXAMPLE X

Preparation of 3-(5-methyl-2-thienyl)methylene]-2.4(3H.5H)-1-thiophen edione 2.2 mmole of thiotetramic acid and 3.3 mmole of 5-methyl-2-thiophenecarboxaldehyde was stirred at 80°–90° C. until all had dissolved (about two minutes). One drop of HCl was added and stirring was continued for 10 minutes at 80°–90° C. The dark solution was cooled and put through a silica plug with $CHCl_3$. Recrystallization from ligroin gave 71% of the analog. The melting point was 49.0°–49.5° C. Molecular formula: $C_{10}H_8O_2S_2$: calculated %C 53.58; %H 3.60; found %C 53.39, %H 3.89. NMR results: 1HNMR (CDCl3/TMS) δ 2.59 (3H, d, 7Hz); 6.82 (1H, m); 7.01 (1H, m); 7.20 (1H, m), 7.93 (2H, m).

EXAMPLE Y

Preparation of 3-[(5-bromo-2-thienyl)methylene]-2.4(3H,5H)-1-thiophene dione 3.4 mmole of thiotetronic acid and 4.9 mmole of 5-bromo-2-thiophenecarboxaldehyde was dissolved in 10 mL of MeOH and heated to 60°–70° C. and stirred for four hours. The solvent was removed and the solid mass was chromatographed using $CHCl_3$ as the eluant. Recrystallization from abs. EtOH gave 58T of compound. The melting point was 188°–193° C. (dec.). Molecular formula: $C_9H_5BrO_2S_2$: calculated %C 37.38; TH 1.74; found %C 37.47; %H 1.91. NMR results: 1HNMR (CDCL3/TMS) δ 3.95 (2H, d, 8Hz); 7.25 (1H, m); 7.76 (1H, m).

EXAMPLE Z

Preparation of 3-(5-bromo-3-methyl-2-thienyl)methylene]-2.4(3H,5H)fur andione 2.4 mmole of tetronic acid and 4.8 mmole of 5-bromo-3-methyl-2-thiophenecarboxaldehyde and 15 mL of abs. EtOH and 2 drops of conc. HCl were stirred at 50° C. for 2.5 hours and then allowed to stand at room temperature overnight and then refluxed another hour. The ethanol was removed in vacuo and the mass was triturated with ligroin and chromatographed with $CHCl_3$. The yellow product was recrystallized with abs. EtOH. The product yield was 36%; M. p. 198°–201° C. (dec.). Molecular formula: $C_{10}H_7BrO_3S$: %C 41.83; %H 2.46; found %C 41.49; %H 2.76. NMR results: 1HNMR (CDCl3/TMS) δ 2.55 (3H, s)); 4.63 (2H, d, 6Hz); 7.12 (1H, m); 8.05 (1H, m).

EXAMPLE AA

Preparation of 3-(5-bromo-3-methyl-2-thienyl)methylene-5.5-dimethyl-, 4(3H) furandione 2.5 mmole of 5,5-dimethyltetronic acid and 4.9 mmole 5-bromo-3-methyl-2-thiophenecarboxaldehyde was stirred with 5 mL abs. EtOH at 75° C. until all had dissolved. Two drops of conc. HCl were added and stirring was continued for 45 minutes. After cooling and removal of the EtOH, the product was dissolved in ether and put through a silica plug. Since the product streaked and overlapped with the starting aldehyde, the product mixture was heated to 120° C. in a kugelrohr. The pot residue was recrystallized from EtOAc/ligroin to give 20T of pure product. M. p. 109°-125° C. (rearrangement to form a red solid). Molecular formula: $C_{12}H_{11}BrO_3S$: calculated %C 45.73; TH 3.52; found %C 46.00; %H 3.54. NMR results: 1HNMR (CDCl$_3$/TMS) 6 1.52 (6H, s); 2.54; 7.11 (1H, d, 2Hz); 7.06 (1H, s).

What is claimed is:

1. A method of treating mammal having cancerous tumor cells with at least one 3-(heteroarylalkylene) 2,4 (3H,5H) furandione for inhibiting or reducing the growth of said cancerous tumor cells, comprising:

injecting or administering orally a 3-(heteroarylalkylene) 2,4 (3H, 5H) furandione into a mammal having cancerous tumor cells at an effective dosage amount for a sufficient time period to inhibit or reduce said growth of said cancerous tumor cells. wherein said at least one 3-(heteroarylalkylene) 2, 4 (3H, 5H) furandione has the general formula:

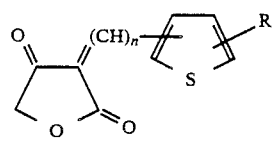

where R represents hydrogen or alkyls containing 1 to 3 carbon atoms or halogens such as chlorine, fluorine, bromine and iodine; and n is 1 or 3.

2. A method of treating mammals having cancerous tumor cells with at least one 3-(heteroarylalkylene) 2,4 (3H, 5H)-furandione for inhibiting or reducing the cancer cell growth, comprising:

injecting or administering orally a 3-(heteroarylalkylene)2, 4 (3H, 5H) furandione into a mammal having cancerous tumor cells at an effective dosage amount for a sufficient time period to inhibit or reduce said cells; wherein said at least one 3-(heteroarylalkylene) 2,4 (3H, 5H) furandione has the general formula:

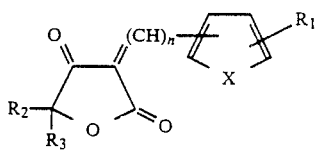

where $R_1$ represents hydrogen, carboxyl, ethoxycarbonyl, methoxy, or alkyls containing one to three carbon atoms such as methyl, ethyl, and propyl; or halogens such as chlorine, fluorine, bromine, and iodine; and $R_2$ and $R_3$ represent independently hydrogen or methyl; and n is 1 or 3.

3. The method of claim 2, wherein said at least one 3-(heteroarylalkylene) 2, 4 (3H, 5H)-furandione is selected from the class consisting of 3[(5-methyl-2-thienyl)methylene]2, 4, (3H, 5H)-furandione; and 3[[3-methyl-2-thienyl]methylene]2, 4, (3H, 5H)-furandione.

4. The method of claim 2, wherein said at least one 3-(heteroarylalkylene) 2, 4 (3H, 5H) -furandione is selected from the class consisting of 3-[(5-piperidyl-2-thienyl)methylene]2,4(3H,5H)-furandione; 3-[(5-ethoxycarbonyl-2-thienyl)methylene]2,4(3H,5H) -furandione;

3-[(5-methyl-2-thienyl)methylene]-(5,5 dimethyl)-2,4(3H,5H) -furandione;

3-[(5iodo-2-thienyl)methylene]-(5,5-dimethyl)-2,4(3H,5H)-furandione;

3-[(5-bromo-2-thienyl)methylene]-(5,5-dimethyl)-2,4(3H,5H)-furandione;

3-[(5-ethoxycarbonyl-2-thienyl)methylene]-(5,5-dimethyl)-2,4(3H,5H) -furandione;

3-[(3-methyl-2-thienyl)methylene]-(5,5-dimethyl)-2,4(3H,5H)-furandione;

3-[(5 methyl-2-thienyl)methylene] 2, 4, (3H, 5H) furandione;

3-[(3-methyl-2-thienyl)methylene] 2, 4, (3H, 5H)-furandione;

3[(5-methyl-2-thienyl)methylene] 2, 4, (3H, 5H) -furandione; and

3[(3-methyl-2-thienyl)methylene] 2, 4, (3H, 5H) -furandione.

* * * * *